(12) United States Patent
Chao et al.

(10) Patent No.: US 11,280,818 B2
(45) Date of Patent: Mar. 22, 2022

(54) AC IMPEDANCE MEASUREMENT CIRCUIT WITH CALIBRATION FUNCTION

(71) Applicant: Hycon Technology Corporation, Taipei (TW)

(72) Inventors: Po-Yin Chao, Taipei (TW); Shui-Chu Lee, Taipei (TW); Yu-Wei Chuang, Taipei (TW)

(73) Assignee: Hycon Technology Corporation, Taipei (TW)

(*) Notice: Subject to any disclaimer, the term of this patent is extended or adjusted under 35 U.S.C. 154(b) by 11 days.

(21) Appl. No.: 16/895,385

(22) Filed: Jun. 8, 2020

(65) Prior Publication Data

US 2021/0382100 A1    Dec. 9, 2021

(51) Int. Cl.
| | |
|---|---|
| *H01L 27/12* | (2006.01) |
| *G01R 27/02* | (2006.01) |
| *G01R 17/10* | (2006.01) |
| *G01R 15/00* | (2006.01) |
| *G01R 35/00* | (2006.01) |

(52) U.S. Cl.
CPC .......... *G01R 27/02* (2013.01); *G01R 15/002* (2013.01); *G01R 17/105* (2013.01); *G01R 35/007* (2013.01)

(58) Field of Classification Search
CPC .... G01R 27/02; G01R 15/002; G01R 17/105; G01R 35/007; G01R 27/00

USPC .......................................................... 324/600
See application file for complete search history.

(56) References Cited

U.S. PATENT DOCUMENTS

| | | | |
|---|---|---|---|
| 7,391,257 B1* | 6/2008 | Denison | A61B 5/7228 330/9 |
| 9,575,105 B1* | 2/2017 | Witt | G01R 27/02 |
| 11,099,700 B1* | 8/2021 | Wang | G06F 3/041661 |
| 2017/0254844 A1* | 9/2017 | Sestok, IV | G01R 27/14 |
| 2021/0288635 A1* | 9/2021 | Wu | H03K 17/082 |

* cited by examiner

*Primary Examiner* — Tung X Nguyen
*Assistant Examiner* — Robert P Alejnikov, Jr.
(74) *Attorney, Agent, or Firm* — Demian K. Jackson; Jackson IPG PLLC (57) ABSTRACT

The present invention discloses an AC impedance measurement circuit with a calibration function, which is characterized in that only one calibration impedance is needed, associated with a switch circuit. Based on the measurement results of the two calibration modes, an equivalent impedance of the switch circuit, circuit gain and phase offset can be calculated. Based on the above results, the equivalent impedance of the internal circuit is deducted from the measurement result of the measurement mode to accurately calculate an AC conductance and a phase of the AC conductance for impedance to be measured. In addition, by adjusting a phase difference between an input sine wave signal and a sampling clock signal, impedance of the same phase and impedance of the quadrature phase can be obtained, respectively, and the AC impedance and phase angle of the impedance to be measured can be calculated.

9 Claims, 9 Drawing Sheets

Fig. 9

AC IMPEDANCE MEASUREMENT CIRCUIT WITH CALIBRATION FUNCTION

FIELD OF THE INVENTION

The present invention relates to an AC impedance measurement circuit. More specifically, the present invention relates to a measurement circuit with a calibration function to calculate an equivalent impedance of a switch circuit in order to compensate measurement result.

BACKGROUND OF THE INVENTION

AC impedance measurement circuits are widely used in human body impedance measurement, allowing users to pay attention to their own body fat content, and then more accurately grasp their own health status. Although DC impedance measurement circuits are simpler, the disadvantage is that the measurement results include human skin impedances, which makes the accuracy of the total impedance measurement result worse. AC impedance measurement circuits can reduce the influence of skin impedance on measurement result, and accurately analyze the equivalent AC impedance and phase characteristics of human body.

Chinese Patent No. 105,662,411 discloses an AC impedance measurement circuit, in which a sinusoidal current generator is used to generate a sinusoidal excitation current, which is applied to both ends of a human body to be tested. An output of a rectifying filter circuit determines an equivalent impedance of the human body.

U.S. Pat. No. 10,551,469 discloses an AC impedance measurement circuit and a calibration circuit in which two calibration impedances are connected in parallel with an object to be measured, and a switch is used to switch to measure the calibration impedance or the impedance of the object to be measured. The measurement result of calibration impedance is calibrated, and thus the accuracy of AC impedance measurement can be improved.

In the above-mentioned prior arts, when the AC impedance measurement circuit is calibrated, it is necessary to connect two calibration impedances, which is inconvenient. In addition, the switch connected in series with the object under test also has an impedance, which will affect the accuracy of the measurement result. Therefore, a more convenient calibration circuit and calibration method are needed to compensate the equivalent impedance of the switch circuit, in order to improve the convenience and the measurement accuracy.

SUMMARY OF THE INVENTION

The present invention discloses An AC impedance measurement circuit, comprising: a waveform generation circuit having a sinusoidal signal output for outputting a sinusoidal signal and a clock signal output for outputting a clock signal; a first amplifier having a positive input and a negative input, the former of which is connected to the sinusoidal signal output; a switch circuit connected to the negative input of the first amplifier and an output of the first amplifier; an impedance to be measured and a calibration impedance, connected to the switch circuit; a second amplifier having a positive input connected to a reference voltage and a negative input connected to the impedance to be measured or the calibration impedance; a reference impedance connected between the negative input of the second amplifier and an output of the second amplifier; and a sampling circuit for receiving the clock signal generated by the waveform generation circuit, connected to both ends of the reference impedance, wherein the switch circuit includes a plurality of switches, and either the impedance to be measured or the calibration impedance is connected between the first amplifier and the second amplifier by controlling the plurality of switches, or the calibration impedance is connected with an additional switch.

In the above-mentioned AC impedance measurement circuit, the switch circuit comprises: a first switch connected between the negative input of the first amplifier and the calibration impedance; a second switch connected between the negative input of the first amplifier and the output of the first amplifier; a third switch connected between the output of the first amplifier and the impedance to be measured; and a fourth switch connected between the output of the first amplifier and the calibration impedance.

The present invention discloses another AC impedance measurement circuit, comprising: a waveform generation circuit having a sinusoidal signal output for outputting a sinusoidal signal and a clock signal output for outputting a clock signal; a reference impedance connected to the sinusoidal signal output directly or through a first amplifier, wherein the first amplifier has a positive input connected to the sinusoidal signal output and a negative input connected to the reference impedance together with an output of the first amplifier; a second amplifier having a positive input connected to a reference voltage and a negative input connected to the reference impedance; a switch circuit, an impedance to be measured and a calibration impedance, connected between the negative input and an output of the second amplifier; and a sampling circuit for receiving the clock signal generated by the waveform generation circuit, connected to the output of the second amplifier, the negative input of the second amplifier, or the switch circuit, wherein the switch circuit includes a plurality of switches, and either the impedance to be measured or the calibration impedance is connected between the negative input and the output of the second amplifier by controlling the plurality of switches, or the calibration impedance is connected with an additional switch.

In the above-mentioned AC impedance measurement circuit, the switch circuit comprises: a first switch having one end connected to the negative input or the output of the second amplifier and other end connected to the calibration impedance; a second switch having one end connected to the negative input or the output of the second amplifier; a third switch connected between the impedance to be measured and other end of the second switch; and a fourth switch having one end connected to the calibration impedance and other end connected to the second switch and the third switch.

The present invention discloses yet another AC impedance measurement circuit, comprising: a waveform generation circuit having a sinusoidal signal output for outputting a sinusoidal signal and a clock signal output for outputting a clock signal; a reference impedance connected to the sinusoidal signal output directly or through a first amplifier, wherein the first amplifier has a positive input connected to the sinusoidal signal output and a negative input connected to the reference impedance together with an output of the first amplifier; a second amplifier having a positive input connected to a reference voltage and a negative input connected to the reference impedance; an impedance to be measured and a calibration impedance, connected to the negative input of the second amplifier; a switch circuit connected between the impedance to be measured or the calibration impedance and an output of the second amplifier;

and a sampling circuit for receiving the clock signal generated by the waveform generation circuit, connected to the output of the second amplifier, the negative input of the second amplifier, or the switch circuit, wherein the switch circuit includes a plurality of switches, and either the impedance to be measured or the calibration impedance is connected between the negative input and the output of the second amplifier by controlling the plurality of switches, or the calibration impedance is connected with an additional switch.

In the above-mentioned AC impedance measurement circuit, the switch circuit comprises: a first switch having one end connected to the negative input or the output of the second amplifier and other end connected to the calibration impedance; a second switch having one end connected to the negative input or the output of the second amplifier; a third switch connected between the impedance to be measured and other end of the second switch; and a fourth switch having one end connected to the calibration impedance and other end connected to the second switch and the third switch.

In the AC impedance measurement circuit according to the present invention, the second switch and the fourth switch are turned on in a first calibration mode; the first switch and the fourth switch are turned on in a second calibration mode; the second switch and the third switch are turned on in a measurement mode; and the fourth switch is turned off in the second calibration mode when the sampling circuit is connected to the negative input and the output of the second amplifier.

In the AC impedance measurement circuit according to the present invention, the waveform generation circuit comprises: a digital waveform synthesis circuit for outputting a digital sinusoidal signal; and a digital-to-analog converter for converting the digital sinusoidal signal into an analog sinusoidal signal.

In the AC impedance measurement circuit according to the present invention, the sampling circuit comprises a digital quantization circuit for converting an analog sampling signal into a digital signal.

In the AC impedance measurement circuit according to the present invention, sampling time of the sampling circuit is controlled by adjusting phase difference between the sinusoidal signal and the clock signal; wherein in-phase sampling or integration result without phase difference is obtained as in-phase value for a signal from the output of the second amplifier, and quadrature phase sampling or integration result with phase difference of 90° is obtained as quadrature phase value for the signal from the output of the second amplifier; wherein the integration results can be obtained either by integrating the sinusoidal signal in a period or by integrating the sinusoidal signal in a first half of a period minus integrating the sinusoidal signal in a second half of a period; and wherein AC conductance value is equal to root of sum of in-phase value square and quadrature phase value square, and AC conductance phase value is equal to arc tangent of quadrature phase value over in-phase value.

In the AC impedance measurement circuit according to the present invention, sampling time of the sampling circuit is controlled by adjusting phase difference between the sinusoidal signal and the clock signal; wherein difference between in-phase sampling or integration result without phase difference and that with phase difference of 180° is obtained as in-phase value for a signal from the output of the second amplifier, and difference between quadrature phase sampling or integration result with phase difference of 90° and that with phase difference 270° of is obtained as quadrature phase value for the signal from the output of the second amplifier; wherein the integration results can be obtained either by integrating the sinusoidal signal in a period or by integrating the sinusoidal signal in a first half of a period minus integrating the sinusoidal signal in a second half of a period; and wherein AC conductance value is equal to root of sum of in-phase value square and quadrature phase value square, and AC conductance phase value is equal to arc tangent of quadrature phase value over in-phase value.

In the AC impedance measurement circuit according to the present invention, an equivalent impedance of the fourth switch is obtained on the basis of difference between the AC conductance values in the first calibration mode and the second calibration mode together with the calibration impedance; wherein a gain is obtained on the basis of a ratio of the calibration impedance or the equivalent impedance of the fourth switch to the AC conductance value; wherein the AC impedance measurement circuit has a phase delay equal to AC conductance phase value in the first calibration mode or AC conductance phase value in the second calibration mode; and wherein the impedance to be measured is obtained by subtracting an equivalent impedance of switch connected in series with the impedance to be measured from AC impedance measurement result in the measurement mode.

In the AC impedance measurement circuit according to the present invention, the equivalent impedance of the fourth switch is equal to the AC conductance value in the second calibration mode divided by the AC conductance value in the first calibration mode, minus 1 and then multiplied by resistance of the calibration impedance, and the gain of the AC impedance measurement circuit is equal to conductance measurement result in the second calibration mode multiplied by the resistance of the calibration impedance; and wherein when the sampling circuit is connected to the negative input and output of the second amplifier, the equivalent impedance of the fourth switch is equal to {the AC conductance value in the second calibration mode minus the AC conductance value in the first calibration mode} divided by {the AC conductance value in first calibration mode times 2 minus the AC conductance value in the second calibration mode} and then multiplied by the resistance of the calibration impedance, and the gain of the AC impedance measurement circuit is equal to the conductance measurement result in the second calibration mode multiplied by {the resistance of the calibration impedance plus the equivalent impedance of the fourth switch}.

This paragraph extracts and compiles some features of the present invention; other features will be disclosed in the follow-up paragraphs. It is intended to cover various modifications and similar arrangements included within the spirit and scope of the appended claims.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

The present invention will be described more specifically with reference to the following embodiments. Please note that the following description of the embodiments of the present invention is limited to the purpose of description. The present invention is not limited to the disclosed forms.

Figure 1:
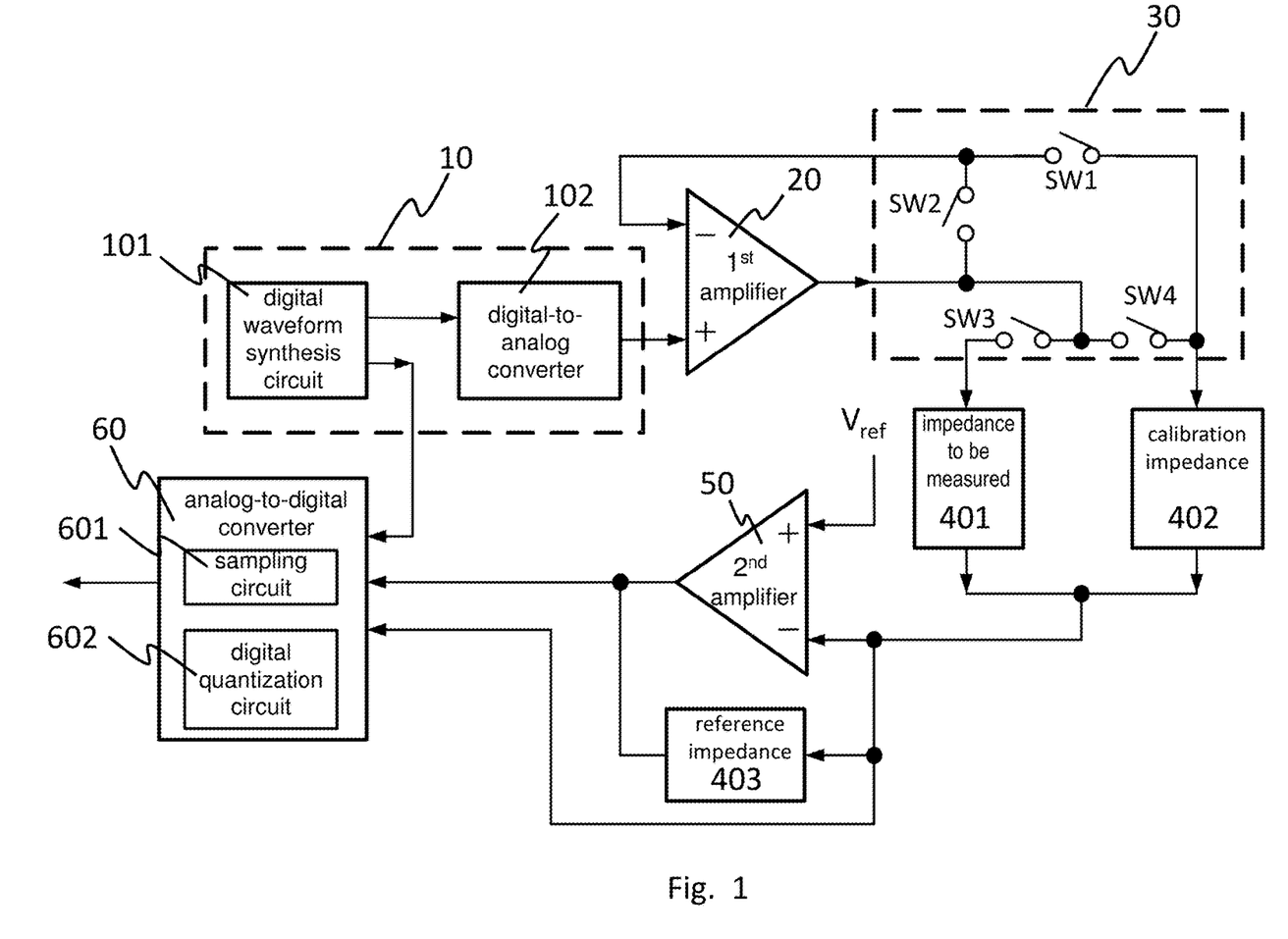
FIG. 1 shows an AC impedance measurement circuit.

FIG. 1 shows a first embodiment of the present invention. An AC impedance measurement circuit comprises: a waveform generation circuit 10 having a sinusoidal signal output for outputting a sinusoidal signal and a clock signal output for outputting a clock signal; a first amplifier 20 having a positive input connected to the sinusoidal signal output; a switch circuit 30 connected to a negative input of the first amplifier 20 and an output of the first amplifier 20; an impedance to be measured 401 and a calibration impedance 402, connected to the switch circuit 30; a second amplifier 50 having a positive input connected to a reference voltage and a negative input connected to the impedance to be measured 401 or the calibration impedance 402; a reference impedance 403 connected between the negative input of the second amplifier 50 and an output of the second amplifier 50; and an analog-to-digital converter 60 connected to the clock signal output of the waveform generation circuit 10 and both ends of the reference impedance 403.

According to the above-mentioned AC impedance measurement circuit, the switch circuit 30 comprises: a first switch SW1 connected between the negative input of the first amplifier 20 and the calibration impedance 402; a second switch SW2 connected between the negative input of the first amplifier 20 and the output of the first amplifier 20; a third switch SW3 connected between the output of the first amplifier 20 and the impedance to be measured 401; and a fourth switch SW4 connected between the output of the first amplifier 20 and the calibration impedance 402. Either the impedance to be measured 401 or the calibration impedance 402 is connected between the first amplifier 20 and the second amplifier 50 by controlling the switches SW1-SW4 or the calibration impedance 402 is connected with an additional switch.

In the switch circuit 30 of the above-mentioned AC impedance measurement circuit, the second switch SW2 and the fourth switch SW4 are turned on in a first calibration mode; the first switch SW1 and the fourth switch SW4 are turned on in a second calibration mode; the second switch SW2 and the third switch SW3 are turned on in a measurement mode.

Figure 2:
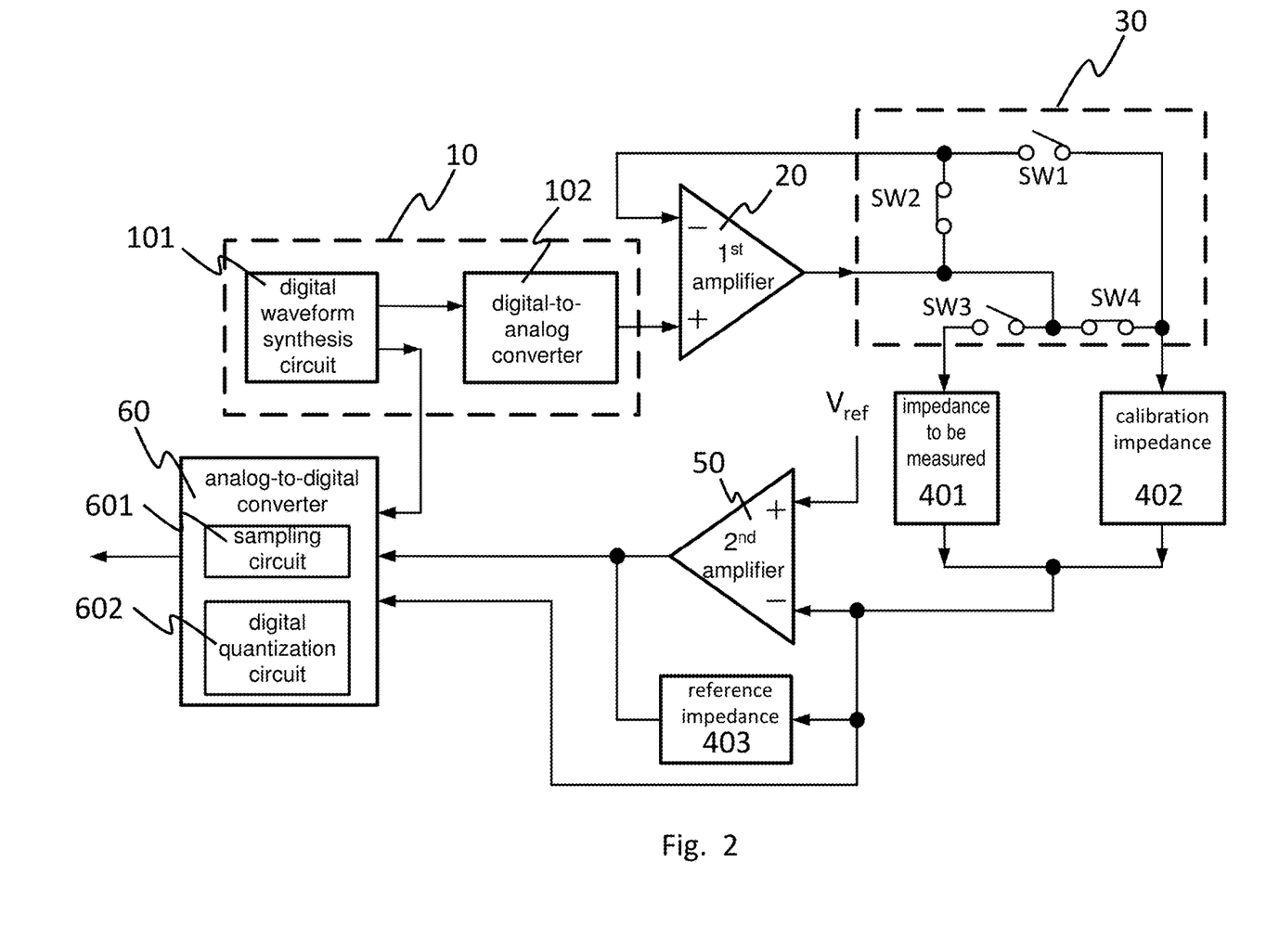
FIG. 2 illustrates conduction of the switches in a first calibration mode for the AC impedance measurement circuit shown in FIG. 1.

In the first calibration mode, as shown in FIG. 2, the second switch SW2 and the fourth switch SW4 are turned on to connect the negative input of the first amplifier 20 to the output of the first amplifier 20 through the second switch SW2, and to connect the calibration impedance 402 to the output of the first amplifier 20 through the fourth switch SW4. In the first calibration mode, the output of the first amplifier 20 and the negative input of the second amplifier 50 are connected with the fourth switch SW4 and the calibration impedance 402 such that the AC impedance measurement circuit can measure equivalent impedance of the fourth switch SW4 and the calibration impedance 402 connected in series.

Figure 3:
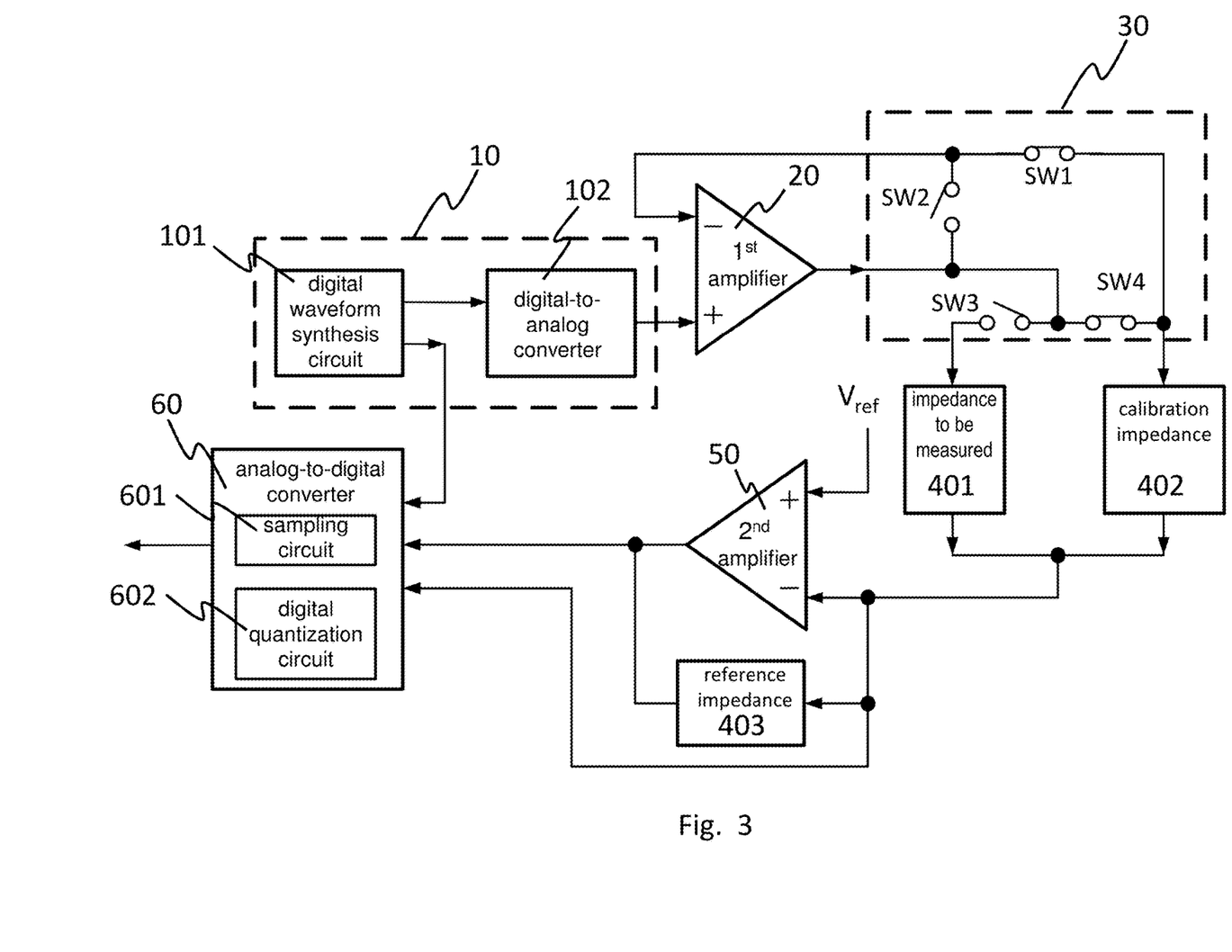
FIG. 3 illustrates conduction of the switches in a second calibration mode for the AC impedance measurement circuit shown in FIG. 1.

In the second calibration mode, as shown in FIG. 3, the first switch SW1 and the fourth switch SW4 are turned on to connect the negative input of the first amplifier 20 to the output of the first amplifier 20 through the first switch SW1 and the fourth switch SW4, and to connect the calibration impedance 402 to the output of the first amplifier 20 through the fourth switch SW4. In the second calibration mode, the first switch SW1 and the fourth switch SW4 are used for the first amplifier 20 such that the AC impedance measurement circuit can measure value of the calibration impedance 402.

Figure 4:
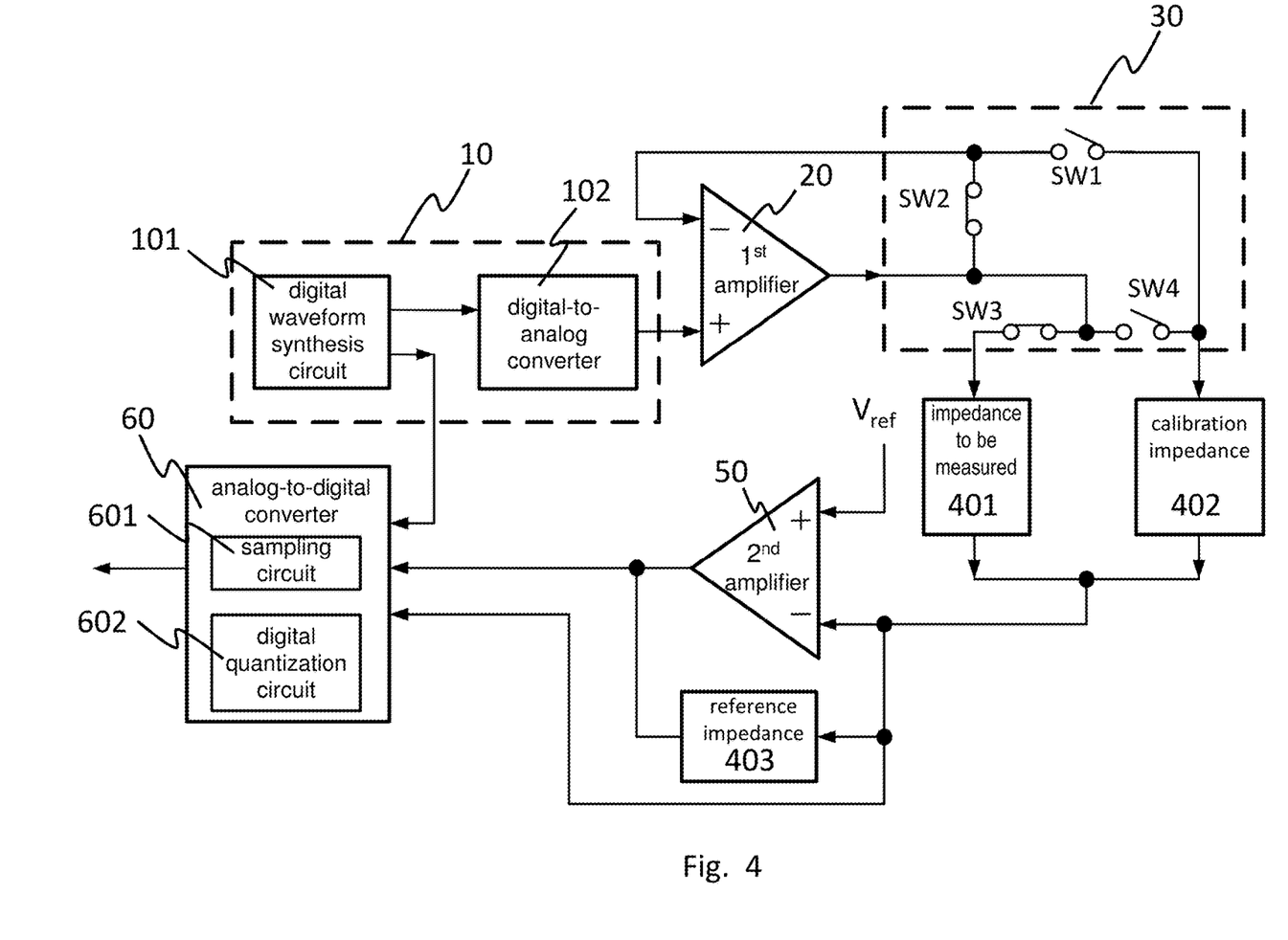
FIG. 4 illustrates conduction of the switches in a measurement mode for the AC impedance measurement circuit shown in FIG. 1.

In the measurement mode, as shown in FIG. 4, the second switch SW2 and the third switch SW3 are turned on to connect the negative input of the first amplifier 20 to the output of the first amplifier 20 through the second switch SW2, and to connect the impedance to be measured 401 to the output of the first amplifier 20 through the third switch SW3. In the measurement mode, equivalent impedance of the third switch SW3 and the impedance to be measured 401 connected in series is measured by the AC impedance measurement circuit.

Figure 5A:
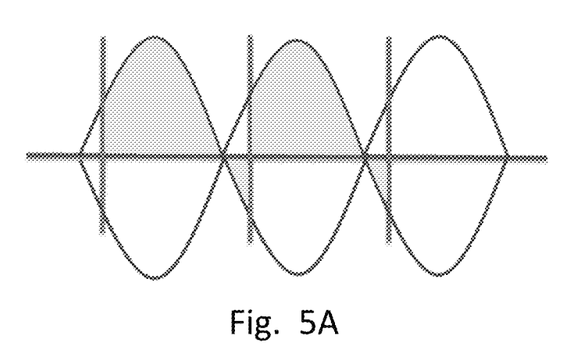
FIGS. 5A to 5D are views showing adjustment of sampling time of the sampling circuit by controlling the clock signal in the AC impedance measurement circuit.

According to the above-mentioned AC impedance measurement circuit, sampling time of the sampling circuit 601 of the analog-to-digital converter 60 is controlled by adjusting phase difference between the sinusoidal signal and the clock signal of the waveform generation circuit 10. In-phase sampling or integration result without phase difference is obtained as in-phase value for a signal from the output of the second amplifier 50, and quadrature phase sampling or integration result with phase difference of 90° is obtained as quadrature phase value for the signal from the output of the second amplifier 50. When the sinusoidal signal generated by the waveform generation circuit 10 goes through the first amplifier 20, the switch circuit 30, the impedance to be measured 401 or the calibration impedance 402, the reference impedance 403 and the second amplifier 20, phase delay upon reception at the sampling circuit 601 is defined as $\Theta$. If there is no phase difference between the sinusoidal signal from the waveform generation circuit 10 and the clock signal, the sampling time of the sampling circuit 601 is synchronous with the sinusoidal signal, and there is phase delay $\Theta$ with the output of the second amplifier 50. The sampling circuit 601 can perform sampling at this time or integration for a full period of the sinusoidal signal, as shown in FIG. 5A. The in-phase sampling or integration result under no phase difference situation is referred to as ADC1.

Figure 5B:
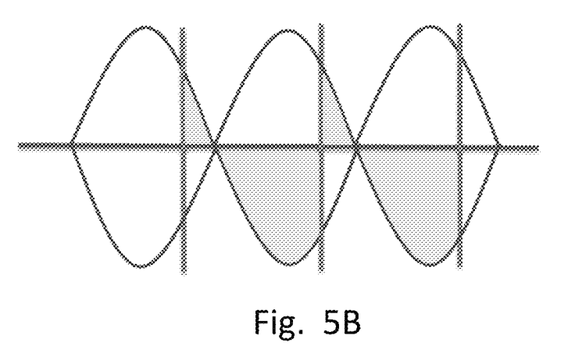

According to the above-mentioned AC impedance measurement circuit, when there is a phase difference of 90° between the sinusoidal signal and the clock signal of the waveform generation circuit 10, sampling time for the sampling circuit 601 is delayed by 90° compared with the sinusoidal signal, and there is a phase delay of $\Theta+90°$ compared with the output of the second amplifier 50. The sampling circuit 601 can perform sampling at this time or integration for a full period of the sinusoidal signal, as shown in FIG. 5B. The quadrature phase sampling or integration result under phase difference of 90° situation is referred to as ADC2.

Figure 5C:
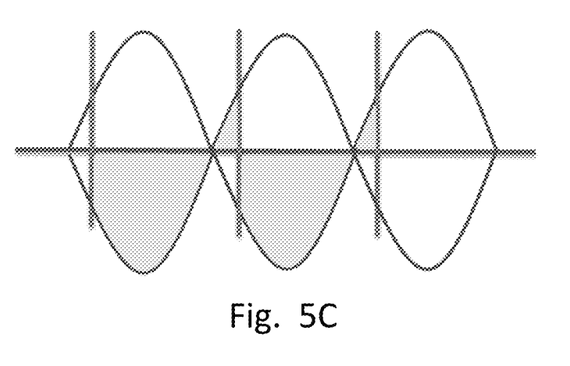
Figure 5D:
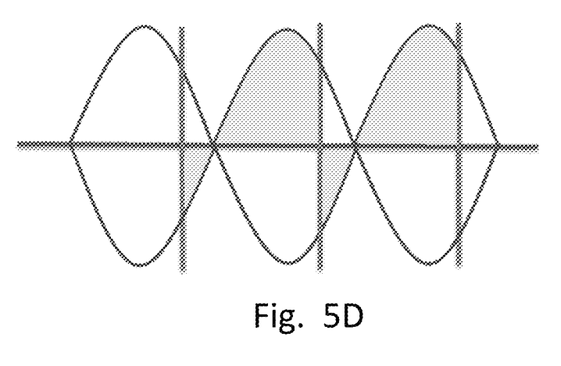

According to the above-mentioned AC impedance measurement circuit, during calculation of in-phase sampling or integration result, a phase difference of 180° between the sinusoidal signal and the clock signal of the waveform generation circuit 10 can be generated. Compared with the sinusoidal signal, the sampling circuit 601 is 180° behind, and there is a phase delay of Θ+180° compared with the output of the second amplifier 50. The sampling circuit 601 performs sampling at this time or integration for a full period, as shown in FIG. 5C. The sampling or integration result is referred to as ADC3. Equation of {(ADC1−ADC3)/2} is used for calculating in-phase sampling or integration result. Similarly, a phase difference of 270° between the sinusoidal signal and the clock signal of the waveform generation circuit 10 can be generated. There is a phase delay of Θ+270° compared with the output of the second amplifier 50. The sampling circuit 601 performs sampling at this time or integration for a full period, as shown in FIG. 5D. The sampling or integration result is referred to as ADC4. Equation of {(ADC2−ADC4)/2} is used for calculating quadrature phase sampling or integration result.

The above-mentioned in-phase sampling or integration result is referred to as 'in-phase value (I)', the quadrature phase sampling or integration result is referred to as 'quadrature phase value (Q)'. The AC conductance value (Y) is equal to root of in-phase value I square plus quadrature phase value Q square: $[Y=(I^2+Q^2)^{0.5}]$. The AC conductance phase value (Θ) is equal to arc tangent of the quadrature phase value divided by the in-phase value: $[\Theta=\tan^{-1}(Q/I)]$.

The integration results can be obtained either by integrating the sinusoidal signal in a period or by integrating the sinusoidal signal in a first half of a period minus integrating the sinusoidal signal in a second half of a period.

According to the above-mentioned AC impedance measurement circuit, the calculation results in the first calibration mode are referred to as Y1 and Θ1, which correspond to equivalent conductance of the calibration impedance 402 and equivalent impedance (referred to as Rs) of the fourth switch SW4 connected in parallel and conductance phase value, respectively. The calculation results in the second calibration mode are referred to as Y2 and Θ2, which correspond to equivalent conductance and conductance phase value of the calibration impedance 402, respectively. According to this embodiment, suppose the calibration impedance 402 to be 5.1K ohm, and then the equivalent impedance Rs of the fourth switch SW4 is $[Rs=5.1K*((Y2/Y1)-1)]$. The gain G is $[G=5.1K*Y2]$.

According to the above-mentioned AC impedance measurement circuit, the calculation results in the measurement mode are referred to as Y3 and Θ3, which correspond to equivalent conductance of the impedance to be measured 401 and equivalent impedance (referred to as Rs) of the third switch SW3 connected in parallel and conductance phase value, respectively. When the equivalent impedance of the third switch SW3 matches that of the fourth switch SW4, the impedance to be measured 401 is obtained by subtracting Rs from the measurement result in the measurement mode. Thus, in-phase value of the equivalent impedance for the impedance to be measured is $[I3=Y3*\cos(\Theta3-\Theta1)-Rs]$, where cos( ) represents cosine function, and quadrature phase value is $[Q3=Y3*\sin(\Theta3)]$, where sin( ) represents sine function. Equivalent serial resistance of the impedance to be measured 401 is $[R3=I3=Y3*\cos(\Theta3)-Rs]$, and equivalent serial capacitance of the impedance to be measured 401 is $[C3=1/(2*\pi*fs*Q3)]$, where fs represents frequency of the sinusoidal signal from the waveform generation circuit 10.

According to the above-mentioned AC impedance measurement circuit, equivalent parallel resistance and capacitance of the impedance to be measured 401 can be obtained. Equivalent conductance is $[Y4=(I3^2+Q3^2)^{0.5}]$, equivalent impedance phase value is $[\Theta4=\tan-1(Q3/I3)]$, in-phase value is $[I4=Y4*\cos(\Theta4)]$, and quadrature phase value is $[Q4=Y4*\sin(\Theta4)]$. Equivalent serial capacitance of the impedance to be measured 401 is $[C4=Q4/(2*\pi*fs)]$, and equivalent serial resistance is $[R4=1/I4]$.

Figure 6:
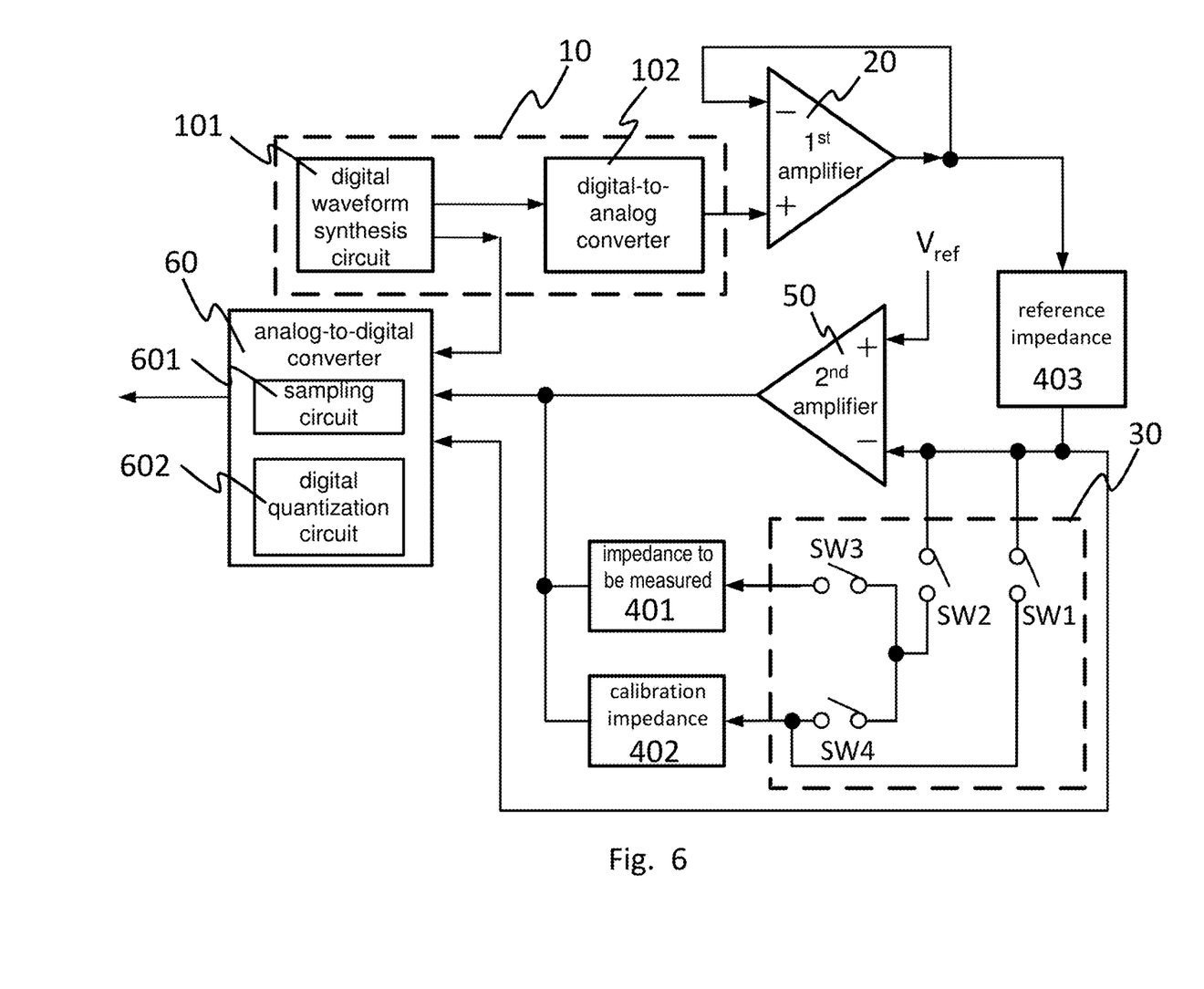
FIG. 6 shows a second AC impedance measurement circuit.

Referring to FIG. 6, which shows a second embodiment of the present invention, another AC impedance measurement circuit comprises: a waveform generation circuit 10 for outputting a sinusoidal signal and a clock signal; a first amplifier 20 having a positive input connected to a sinusoidal signal output of the waveform generation circuit 10 and a negative input connected to a reference impedance 403 together with an output of the first amplifier 20; the reference impedance 403 having other end connected to a switch circuit 30 and a negative input of a second amplifier 50; the second amplifier 50 having a positive input connected to a reference voltage; an impedance to be measured 401 and a calibration impedance 402 connected between the switch circuit 30 and an output of the second amplifier 50; and an analog-to-digital converter 60 for receiving the clock signal of the waveform generation circuit 10, output of the second amplifier 50, and voltage at the negative input of the second amplifier 50.

According to the above-mentioned AC impedance measurement circuit, the switch circuit 30 comprises: a first switch SW1 connected between the negative input of the second amplifier 50 and the calibration impedance 402; a second switch SW2 having one end connected between the negative input of the second amplifier 50 and other end connected with a third switch SW3 and a fourth switch SW4; the third switch SW3 having other end connected to the impedance to be measured 401; and the fourth switch SW4 having other end connected to the calibration impedance 402. Either the impedance to be measured 401 or the calibration impedance 402 is connected between the negative input of the second amplifier 50 and the output of the second amplifier 50 by controlling the switches SW1-SW4 or the calibration impedance 402 is connected with an additional switch.

According to the above-mentioned AC impedance measurement circuit, in the switch circuit 30, the second switch SW2 and the fourth switch SW4 are turned on in a first calibration mode, the first switch SW1 is turned on in a second calibration mode, and the second switch SW2 and the third switch SW3 are turned in a measurement mode.

In the first calibration mode, the second switch SW2 and the fourth switch SW4 are turned on to connect the negative input of the second amplifier 50 to the calibration impedance 402 through the second switch SW2 and the fourth switch SW4. In the first calibration mode, the output of the second amplifier 50 and the negative input of the second amplifier 50 are connected with the second switch SW2, the fourth switch SW4 and the calibration impedance 402 such that the AC impedance measurement circuit can measure equivalent impedance of the second switch SW2, the fourth switch SW4 and the calibration impedance 402 connected in series.

In the second calibration mode, only the first switch SW1 is turned on, and the negative input of the second amplifier 50 is connected to the calibration impedance 402 through the first switch SW1. In the second calibration mode, the AC impedance measurement circuit measures equivalent impedance of the first switch SW1 and the calibration impedance 402 connected in series.

In the measurement mode, the second switch SW2 and the third switch SW3 are turned on to connect the negative input of the second amplifier 50 to the impedance to be measured 401 through the second switch SW2 and the third switch SW3. In the measurement mode, the AC impedance measurement circuit measures equivalent impedance of the second switch SW2, the third switch SW3 and the calibration impedance 402 connected in series.

According to the above-mentioned AC impedance measurement circuit, procedures for calculating sampling or integration results for in-phase and quadrature phase are the same as those described in the first embodiment, and procedures for calculating AC conductance value (Y) and AC conductance phase value (θ) are the same as those described in the first embodiment.

According to the above-mentioned AC impedance measurement circuit, the calculation results in the first calibration mode are referred to as Y1 and Θ1, which correspond to equivalent conductance of the calibration impedance 402, the second switch SW2 and the fourth switch SW4 connected in parallel and conductance phase value, respectively. The calculation results in the second calibration mode are referred to as Y2 and Θ2, which correspond to equivalent conductance and conductance phase value of the calibration impedance 402 and the first switch SW1 connected in parallel, respectively. In comparison with the first embodiment, according to the first calibration mode and the second calibration mode of the second embodiment, an additional switch (SW1 or SW2) is connected in series to measure the calibration impedance 402. Thus, calculations are changed as follows. In the second embodiment, suppose the calibration impedance 402 to be 5.1K ohm and both equivalent impedances of the second switch SW2 and the fourth switch SW4 are Rs, and then Rs is [Rs=5.1K*(Y2−Y1)/(2Y1−Y2)]. The gain G is [G=(5.1K+Rs)*Y2].

In the second embodiment, the calculation results Y3 and Θ3 in the measurement mode correspond to equivalent conductance and conductance phase value of the impedance to be measured 401, the second switch SW2 and the third switch SW3 connected in parallel. In case that the equivalent impedances of the switches (SW1-SW4)) match each other (referred to as Rs), the impedance to be measured 401 is obtained by deducting 2*Rs from the measurement result in the measurement mode. Therefore, in-phase value of the equivalent impedance for the impedance to be measured is [I3=Y3*cos(Θ3−Θ1)−2*Rs], and quadrature phase value is [Q3=Y3*sin(Θ3)]. Equivalent serial resistance of the impedance to be measured 401 is [R3=I3=Y3*cos(Θ3)−2*Rs], and equivalent serial capacitance of the impedance to be measured 401 is [C3=1/(2*π*fs*Q3)].

In the second embodiment, equivalent parallel resistance and capacitance and equivalent serial resistance and capacitance of the impedance to be measured 401 can be obtained as in the first embodiment.

Figure 7:
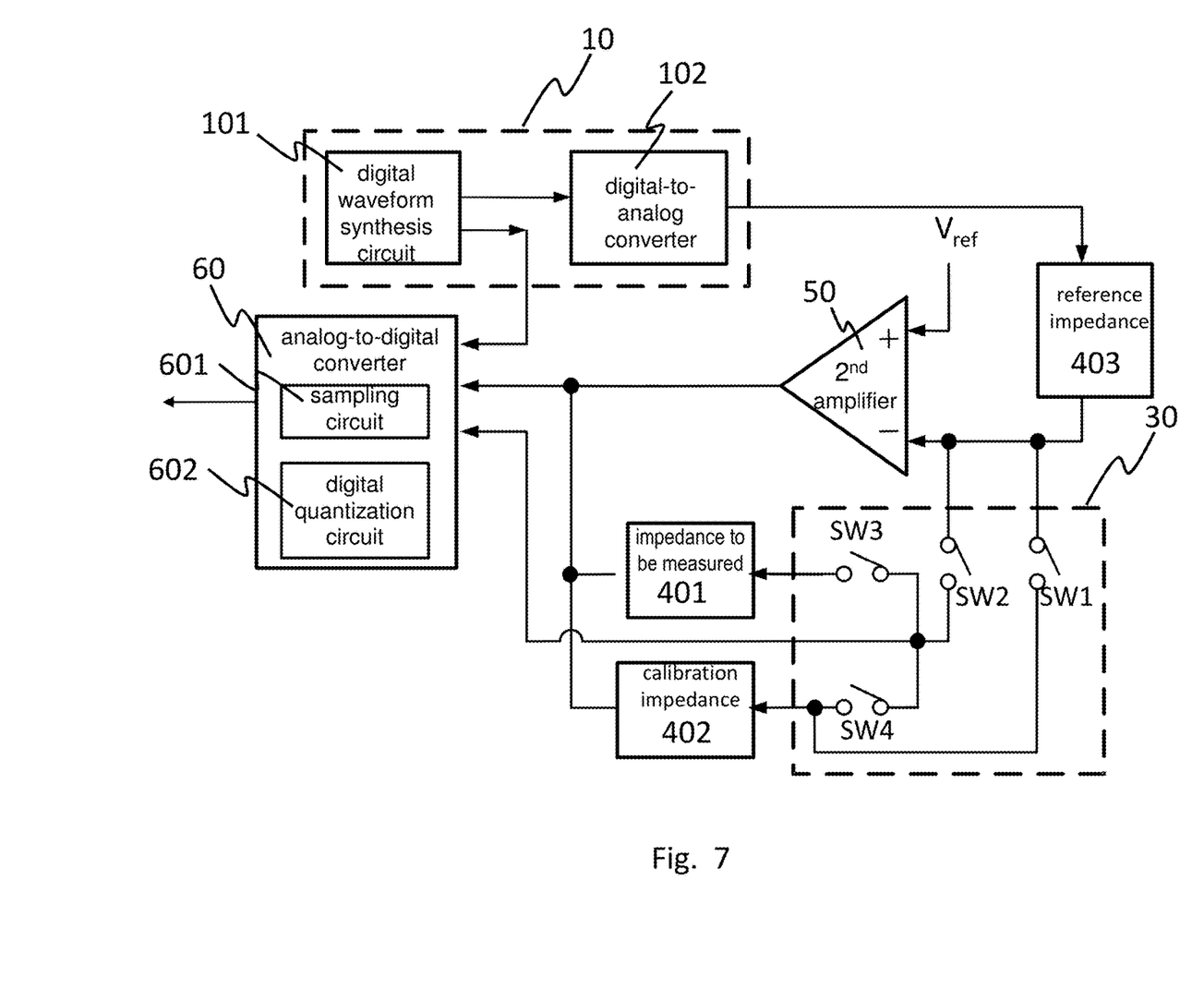
FIG. 7 shows a third AC impedance measurement circuit.

Referring to FIG. 7, which shows a third embodiment of the present invention, yet another AC impedance measurement circuit comprises: a waveform generation circuit 10 for outputting a sinusoidal signal and a clock signal; a reference impedance 403 having one end connected to a sinusoidal signal output of the waveform generation circuit 10 and other end connected to a switch circuit 30 and a negative input of a second amplifier 50; the second amplifier 50 having a positive input connected to a reference voltage; an impedance to be measured and a calibration impedance connected between the switch circuit 30 and an output of the second amplifier 50; and an analog-to-digital converter 60 for receiving the clock signal of the waveform generation circuit 10, output of the second amplifier 50, and voltage from the switch circuit 30.

According to the above-mentioned AC impedance measurement circuit, the switch circuit 30 comprises: a first switch SW1 connected between a negative input of the second amplifier 50 and the calibration impedance 402 之間; a second switch SW2 having one end connected with the negative input of the second amplifier 50 and other end connected with a third switch SW3 and a fourth switch SW4; the third switch SW3 having other end connected with the impedance to be measured 401; and the fourth switch SW4 having other end connected with the calibration impedance 402. The analog-to-digital converter 60, the second switch SW2, the third switch SW3 and the fourth switch SW4 are connected together. Either the impedance to be measured 401 or the calibration impedance 402 is connected between the negative input of the second amplifier 50 and the output of the second amplifier 50 by controlling the switches SW1-SW4 or the calibration impedance 402 is connected with an additional switch.

According to the above-mentioned AC impedance measurement circuit, in the switch circuit 30, the second switch SW2 and the fourth switch SW4 are turned on in a first calibration mode, the first switch SW1 is turned in a second calibration mode, and the second switch SW2 and the third switch SW3 are turned on in a measurement mode.

In the first calibration mode, the second switch SW2 and the fourth switch SW4 are turned on to connect the negative input of the second amplifier 50 to the calibration impedance 402 through the second switch SW2 and the fourth switch SW4. In the first calibration mode, the AC impedance measurement circuit measures equivalent impedance of the fourth switch SW4 and the calibration impedance 402 connected in series.

In the second calibration mode, the first switch SW1 and the fourth switch SW4 are turned on to connect the negative input of the second amplifier 50 to the calibration impedance 402 through the first switch SW1. In the second calibration mode, the AC impedance measurement circuit measures equivalent impedance of the first switch SW1 and the calibration impedance 402 connected in series. The fourth switch SW4 is a path for the analog-to-digital converter 60 to receive voltage, and its equivalent impedance does not substantially affect the measurement result.

In the measurement mode, the second switch SW2 and the third switch SW3 are turned on to connect the negative input of the second amplifier 50 to the impedance to be measured 401 through the second switch SW2. In the measurement mode, AC impedance measurement circuit measures equivalent impedance of the third switch SW3 and the calibration impedance 402 connected in series.

In the third embodiment, calculations of in-phase value (I), quadrature phase value (Q), AC conductance value (Y), AC conductance phase value (Θ), equivalent impedance Rs, gain G, and in-phase value (I3), quadrature phase value (Q3), equivalent serial resistance (R3), equivalent serial capacitance (C3), equivalent parallel resistance (R4), and equivalent parallel capacitance (C4) of equivalent impedance of the impedance to be measured 401 are the same as in the first embodiment.

Figure 8:
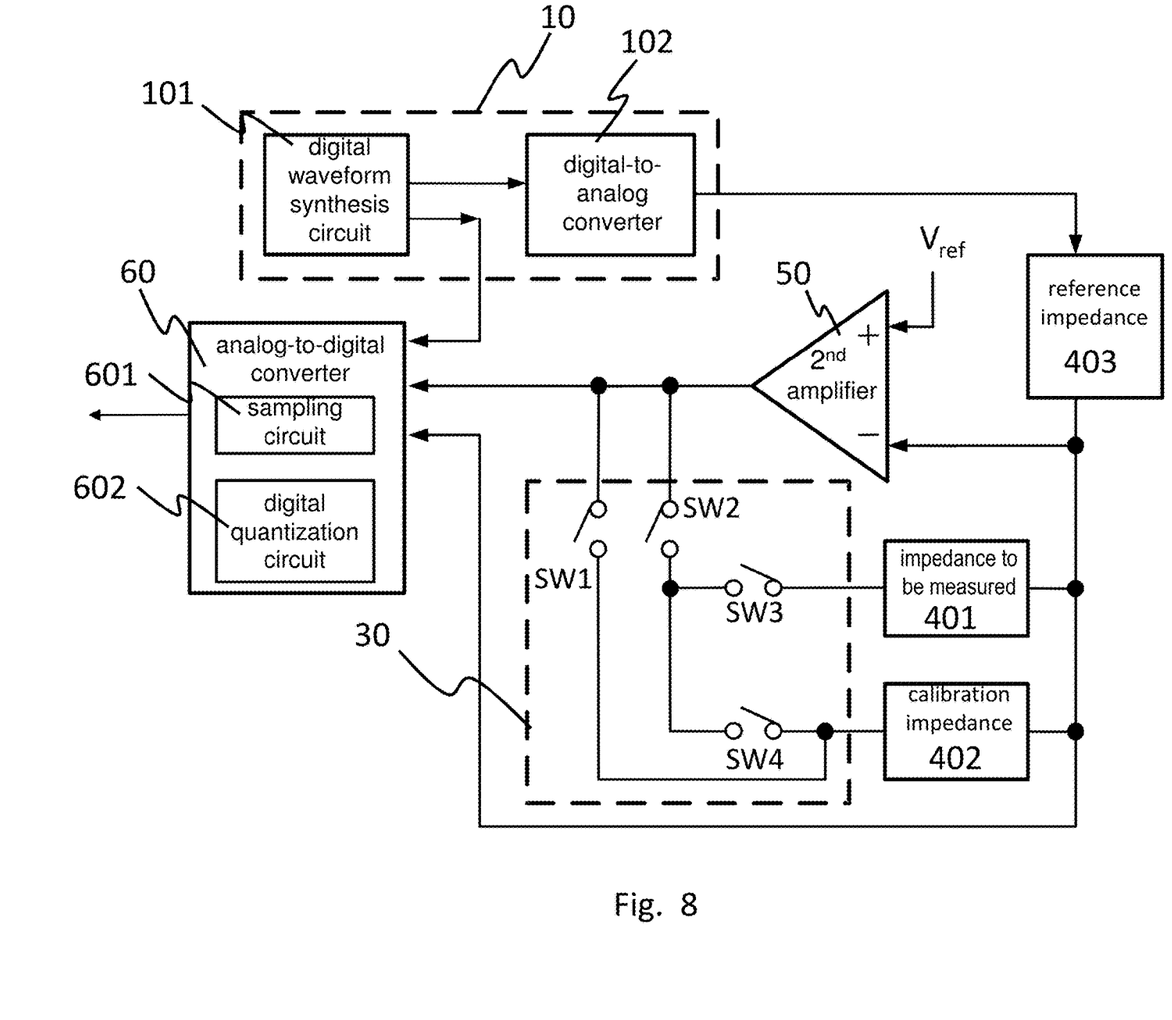
FIG. 8 shows a fourth AC impedance measurement circuit.

Referring to FIG. 8, which shows a fourth embodiment of the present invention, yet another AC impedance measurement circuit comprises: a waveform generation circuit 10 for outputting a sinusoidal signal and a clock signal; a reference impedance 403 having one end connected to a sinusoidal signal output of the waveform generation circuit 10 and other end connected to a negative input of a second amplifier 50, connected with an impedance to be measured 401 and a calibration impedance 402; the second amplifier 50 having a positive input connected to a reference voltage; the impedance to be measured 401 and the calibration impedance 402 having other end connected with a switch circuit 30; the switch circuit 30 connected with an output of the second amplifier 50; and an analog-to-digital converter 60 for receiving the clock signal from the waveform generation circuit 10, output from the second amplifier 50, and voltage at the negative input of the second amplifier 50.

According to the above-mentioned AC impedance measurement circuit, the switch circuit 30 comprises: a first switch SW1 connected between the output of the second amplifier 50 and the calibration impedance 402; a second switch SW2 having one end connected with the output of the second amplifier 50 and other end connected with a third switch SW3 and a fourth switch SW4; the third switch SW3 having other end connected with the impedance to be measured 401; and the fourth switch SW4 having other end connected with the calibration impedance 402. Either the impedance to be measured 401 or the calibration impedance 402 is connected between the negative input of the second amplifier 50 and the output of the second amplifier 50 by controlling the switches SW1-SW4 or the calibration impedance 402 is connected with an additional switch.

According to the above-mentioned AC impedance measurement circuit, in the switch circuit 30, the second switch SW2 and the fourth switch SW4 are turned on in a first calibration mode, the first switch SW1 is turned on in a second calibration mode, and the second switch SW2 and the third switch SW3 are turned on in a measurement mode.

In the first calibration mode, the second switch SW2 and the fourth switch SW4 are turned on to connect the output of the second amplifier 50 to the calibration impedance 402 through the second switch SW2 and the fourth switch SW4. In the first calibration mode, the AC impedance measurement circuit measures equivalent impedance of the second switch SW2, the fourth switch SW4 and the calibration impedance 402 connected in series.

In the second calibration mode, the first switch SW1 is turned on to connect the output of the second amplifier 50 to the calibration impedance 402 through the first switch SW1. In the second calibration mode, the AC impedance measurement circuit measures equivalent impedance of the first switch SW1 and the calibration impedance 402 connected in series.

In the measurement mode, the second switch SW2 and the third switch SW3 are turned on to connect the output of the second amplifier 50 to the impedance to be measured 401 through the second switch SW2 and the third switch SW3. In the measurement mode, the AC impedance measurement circuit measures equivalent impedance of the second switch SW3, the third switch SW3 and the calibration impedance 402 connected in series.

In the fourth embodiment, calculations of in-phase value (I), quadrature phase value (Q), AC conductance value (Y), AC conductance phase value (Θ), equivalent impedance Rs, gain G, and in-phase value (I3), quadrature phase value (Q3), equivalent serial resistance (R3), equivalent serial capacitance (C3), equivalent parallel resistance (R4), and equivalent parallel capacitance (C4) of equivalent impedance of the impedance to be measured 401 are the same as in the second embodiment.

Figure 9:
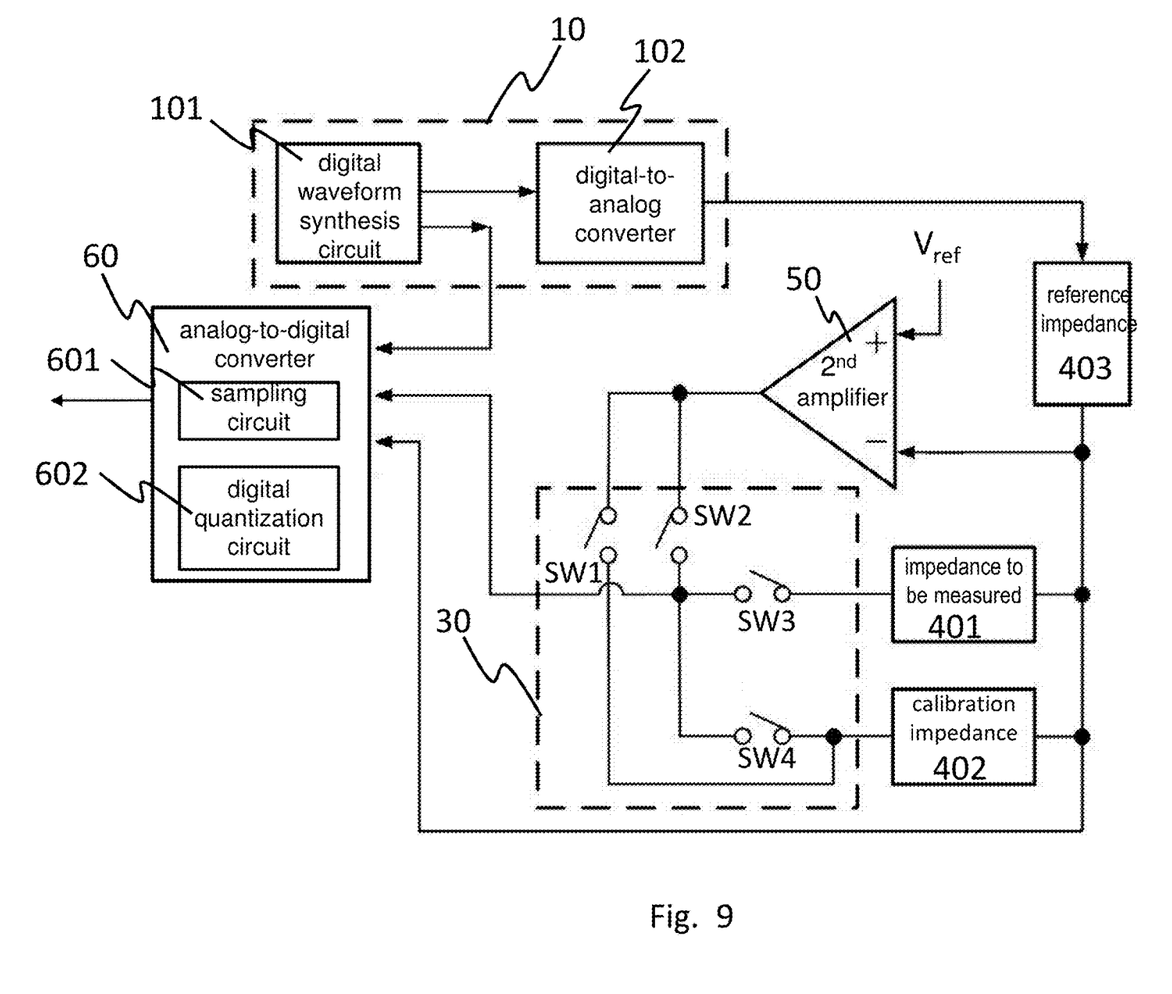
FIG. 9 shows a fifth AC impedance measurement circuit.

Referring to FIG. 9, which shows a fifth embodiment of the present invention, yet another AC impedance measurement circuit as shown is similar to that in the fourth embodiment. The difference is that the output of the second amplifier 50 according to the fourth embodiment is connected to the analog-to-digital converter 60, while in the switch circuit 30 according to the fifth embodiment, the second switch SW2, the third switch SW3 and the fourth switch SW4 are connected to the analog-to-digital converter 60. Calculations of in-phase value (I), quadrature phase value (Q) and so on are the same as in the third embodiment.

According to the above-mentioned AC impedance measurement circuit, the waveform generation circuit 10 comprises a digital waveform synthesis circuit 101 for outputting a digital sinusoidal signal and a digital-to-analog converter 102 for converting the digital sinusoidal signal into an analog sinusoidal signal.

According to the above-mentioned AC impedance measurement circuit, the analog-to-digital converter 60 further comprises a digital quantization circuit 602 for converting analog sampling or integration result into a digital signal for used in the calculations mentioned above.

According to the above-mentioned AC impedance measurement circuit, the reference voltage connected with the negative input of the second amplifier 50 is the same as average voltage of the sinusoidal signal of the waveform generation circuit. For example, if the sinusoidal signal is an AC signal having a voltage between 0V to 5V, the reference voltage is 2.5V.

While the invention has been described in terms of what is presently considered to be the most practical and preferred embodiments, it is to be understood that the invention needs not be limited to the disclosed embodiments. For example, alphanumeric labeling for the steps of the present invention is for the purpose of easy understanding. It is by no means to limit the sequence of the steps. On the contrary, it is intended to cover various modifications and similar arrangements included within the spirit and scope of the appended claims, which are to be accorded with the broadest interpretation so as to encompass all such modifications and similar structures.

What is claimed is:

1. An AC impedance measurement circuit, comprising:
   a waveform generation circuit having a sinusoidal signal output for outputting a sinusoidal signal and a clock signal output for outputting a clock signal;
   a first amplifier having a positive input and a negative input, the former of which is connected to the sinusoidal signal output;
   a switch circuit connected to the negative input of the first amplifier and an output of the first amplifier;
   an impedance to be measured and a calibration impedance, connected to the switch circuit;
   a second amplifier having a positive input connected to a reference voltage and a negative input connected to the impedance to be measured and the calibration impedance;
   a reference impedance connected between the negative input of the second amplifier and an output of the second amplifier; and
   a sampling circuit for receiving the clock signal generated by the waveform generation circuit, connected to both ends of the reference impedance,
   wherein the switch circuit includes a plurality of switches, and either the impedance to be measured or the calibration impedance is connected between the first amplifier and the second amplifier by controlling the plurality of switches, or the calibration impedance is connected with one of the plurality of switches of the switch circuit.

2. The AC impedance measurement circuit according to claim 1, wherein the switch circuit comprises:
   a first switch connected between the negative input of the first amplifier and the calibration impedance;
   a second switch connected between the negative input of the first amplifier and the output of the first amplifier;
   a third switch connected between the output of the first amplifier and the impedance to be measured; and
   a fourth switch connected between the output of the first amplifier and the calibration impedance.

3. The AC impedance measurement circuit according to claim 2, wherein the second switch and the fourth switch are turned on in a first calibration mode; the first switch and the fourth switch are turned on in a second calibration mode; the second switch and the third switch are turned on in a measurement mode; and the fourth switch is turned off in the second calibration mode when the sampling circuit is connected to the negative input and the output of the second amplifier.

4. The AC impedance measurement circuit according to claim 3, wherein an equivalent impedance of the fourth switch is obtained on the basis of difference between the AC conductance values in the first calibration mode and the second calibration mode together with the calibration impedance; wherein a gain is obtained on the basis of a ratio of the calibration impedance or the equivalent impedance of the fourth switch to the AC conductance value; wherein the AC impedance measurement circuit has a phase delay equal to AC conductance phase value in the first calibration mode or AC conductance phase value in the second calibration mode; and wherein the impedance to be measured is obtained by subtracting an equivalent impedance of switch connected in series with the impedance to be measured from AC impedance measurement result in the measurement mode.

5. The AC impedance measurement circuit according to claim 4, wherein the equivalent impedance of the fourth switch is equal to the AC conductance value in the second calibration mode divided by the AC conductance value in the first calibration mode, minus 1 and then multiplied by resistance of the calibration impedance, and the gain of the AC impedance measurement circuit is equal to conductance measurement result in the second calibration mode multiplied by the resistance of the calibration impedance; and wherein when the sampling circuit is connected to the negative input and output of the second amplifier, the equivalent impedance of the fourth switch is equal to {the AC conductance value in the second calibration mode minus the AC conductance value in the first calibration mode} divided by {the AC conductance value in first calibration mode times 2 minus the AC conductance value in the second calibration mode} and then multiplied by the resistance of the calibration impedance, and the gain of the AC impedance measurement circuit is equal to the conductance measurement result in the second calibration mode multiplied by {the resistance of the calibration impedance plus the equivalent impedance of the fourth switch}.

6. The AC impedance measurement circuit according to claim 1, wherein the waveform generation circuit comprises:
   a digital waveform synthesis circuit for outputting a digital sinusoidal signal; and
   a digital-to-analog converter for converting the digital sinusoidal signal into an analog sinusoidal signal.

7. The AC impedance measurement circuit according to claim 1, wherein the sampling circuit comprises a digital quantization circuit for converting an analog sampling signal into a digital signal.

8. The AC impedance measurement circuit according to claim 1, wherein sampling time of the sampling circuit is controlled by adjusting phase difference between the sinusoidal signal and the clock signal; wherein in-phase sampling or integration result without phase difference is obtained as in-phase value for a signal from the output of the second amplifier, and quadrature phase sampling or integration result with phase difference of 90° is obtained as quadrature phase value for the signal from the output of the second amplifier; wherein the integration results can be obtained either by integrating the sinusoidal signal in a period or by integrating the sinusoidal signal in a first half of a period minus integrating the sinusoidal signal in a second half of a period; and wherein AC conductance value is equal to root of sum of in-phase value square and quadrature phase value square, and AC conductance phase value is equal to arc tangent of quadrature phase value over in-phase value.

9. The AC impedance measurement circuit according to claim 1, wherein sampling time of the sampling circuit is controlled by adjusting phase difference between the sinusoidal signal and the clock signal; wherein difference between in-phase sampling or integration result without phase difference and that with phase difference of 180° is obtained as in-phase value for a signal from the output of the second amplifier, and difference between quadrature phase sampling or integration result with phase difference of 90° and that with phase difference 270° of is obtained as quadrature phase value for the signal from the output of the second amplifier; wherein the integration results can be obtained either by integrating the sinusoidal signal in a period or by integrating the sinusoidal signal in a first half of a period minus integrating the sinusoidal signal in a second half of a period; and wherein AC conductance value is equal to root of sum of in-phase value square and quadrature phase value square, and AC conductance phase value is equal to arc tangent of quadrature phase value over in-phase value.

* * * * *